(12) United States Patent
Gross et al.

(10) Patent No.: US 7,833,176 B2
(45) Date of Patent: Nov. 16, 2010

(54) PRESSURE-PROPELLED SYSTEM FOR BODY LUMEN

(75) Inventors: Yosef Gross, Moshav Mazor (IL); Oz Cabiri, Macabim (IL)

(73) Assignee: G. I. View Ltd., Ramat Gan (IL)

( * ) Notice: Subject to any disclaimer, the term of this patent is extended or adjusted under 35 U.S.C. 154(b) by 1331 days.

(21) Appl. No.: 10/753,424

(22) Filed: Jan. 9, 2004

(65) Prior Publication Data

US 2005/0038335 A1    Feb. 17, 2005

(51) Int. Cl.
A61M 25/00 (2006.01)
A61B 1/00 (2006.01)
A61B 1/04 (2006.01)

(52) U.S. Cl. .................. 600/585; 600/104; 600/116
(58) Field of Classification Search .................. 600/585, 600/104, 424, 116; 604/95.03
See application file for complete search history.

(56) References Cited

U.S. PATENT DOCUMENTS

| | | |
|---|---|---|
| 3,895,637 A | 7/1975 | Choy |
| 3,924,625 A | 12/1975 | Peterson |
| 4,040,413 A | 8/1977 | Ohshiro |
| 4,066,070 A | 1/1978 | Utsugi |
| 4,077,610 A | 3/1978 | Masuda |
| 4,148,307 A | 4/1979 | Utsugi |
| 4,176,662 A | 12/1979 | Frazer |
| 4,403,985 A | 9/1983 | Boretos |
| 4,530,698 A | 7/1985 | Goldstein et al. |
| 4,561,427 A | 12/1985 | Takada |
| 4,596,381 A | 6/1986 | Hamrick |
| 4,690,131 A | 9/1987 | Lyddy et al. |
| 4,838,859 A | 6/1989 | Strassmann |
| 4,971,034 A | 11/1990 | Doi et al. |
| 4,976,524 A | 12/1990 | Chiba |
| 5,259,364 A | 11/1993 | Bob et al. |
| 5,337,732 A | 8/1994 | Grundfest et al. |
| 5,353,807 A | 10/1994 | DeMarco |
| 5,364,353 A | 11/1994 | Corfitsen et al. |
| 5,395,332 A | 3/1995 | Ressemann et al. |
| 5,398,670 A | 3/1995 | Ortiz et al. |
| 5,471,988 A | 12/1995 | Fujio et al. |
| 5,509,371 A | 4/1996 | Phillips |

(Continued)

FOREIGN PATENT DOCUMENTS

EP    0242428    10/1987

(Continued)

OTHER PUBLICATIONS

U.S. Appl. No. 60/490,038.

*Primary Examiner*—Max Hindenburg
*Assistant Examiner*—Jeffrey G Hoekstra
(74) *Attorney, Agent, or Firm*—Frommer Lawrence & Haug LLP; William S. Frommer

(57) ABSTRACT

A system including a guide member at least partially insertable into a proximal opening of a body lumen, the guide member including a first passageway connectable to a source of fluid pressure, an elongate carrier arranged for sliding movement through the guide member, and a piston head mounted on the carrier, wherein a greater fluid pressure acting on a proximal side of the piston head than on a distal side of the piston head propels the piston head and the carrier in a distal direction in the body lumen.

11 Claims, 3 Drawing Sheets

U.S. PATENT DOCUMENTS

| | | |
|---|---|---|
| 5,571,114 A | 11/1996 | Devanaboyina |
| 5,586,968 A | 12/1996 | Grundl et al. |
| 5,604,531 A | 2/1997 | Iddan et al. |
| 5,662,587 A | 9/1997 | Grundfest et al. |
| 5,728,068 A | 3/1998 | Leone et al. |
| 5,740,808 A | 4/1998 | Panescu et al. |
| 5,863,284 A | 1/1999 | Klein |
| 5,879,325 A | 3/1999 | Lindstrom et al. |
| 5,906,357 A | 5/1999 | Munson, Sr. |
| 5,906,591 A | 5/1999 | Dario et al. |
| 5,910,105 A | 6/1999 | Swain et al. |
| 5,941,815 A | 8/1999 | Chang |
| 5,984,860 A | 11/1999 | Shan |
| 6,007,482 A | 12/1999 | Madni et al. |
| 6,028,719 A | 2/2000 | Beckstead et al. |
| 6,071,234 A | 6/2000 | Takada |
| 6,157,018 A | 12/2000 | Ishiguro et al. |
| 6,277,065 B1 | 8/2001 | Donofrio |
| 6,296,608 B1 | 10/2001 | Daniels et al. |
| 6,315,713 B1 | 11/2001 | Takada |
| 6,332,865 B1 | 12/2001 | Begg et al. |
| 6,333,826 B1 | 12/2001 | Charles |
| 6,341,044 B1 | 1/2002 | Driscoll, Jr. et al. |
| 6,356,296 B1 | 3/2002 | Driscoll, Jr. et al. |
| 6,373,642 B1 | 4/2002 | Wallerstein et al. |
| 6,388,820 B1 | 5/2002 | Wallerstein et al. |
| 6,422,989 B1 | 7/2002 | Hektner |
| 6,424,377 B1 | 7/2002 | Driscoll, Jr. et al. |
| 6,449,103 B1 | 9/2002 | Charles |
| 6,459,451 B2 | 10/2002 | Driscoll, Jr. et al. |
| 6,485,409 B1 | 11/2002 | Voloshin et al. |
| 6,493,032 B1 | 12/2002 | Wallerstein et al. |
| 6,503,192 B1 | 1/2003 | Ouchi |
| 6,517,477 B1 | 2/2003 | Wendlandt |
| 6,527,705 B1 | 3/2003 | Ouchi |
| 6,537,206 B2 | 3/2003 | Takada |
| 6,544,216 B1 | 4/2003 | Sammler et al. |
| 6,597,520 B2 | 7/2003 | Wallerstein et al. |
| 6,599,237 B1 | 7/2003 | Singh |
| 6,611,282 B1 | 8/2003 | Trubko et al. |
| 6,648,814 B2 | 11/2003 | Kim et al. |
| 6,682,479 B1 | 1/2004 | Takahashi et al. |
| 6,695,771 B2 | 2/2004 | Takada |
| 6,702,734 B2 | 3/2004 | Kim et al. |
| 6,702,735 B2 | 3/2004 | Kelly |
| 6,704,148 B2 | 3/2004 | Kumata |
| 6,709,388 B2 | 3/2004 | Mosse et al. |
| 6,743,208 B1 | 6/2004 | Coyle |
| 6,764,441 B2 | 7/2004 | Chiel et al. |
| 6,786,864 B2 | 9/2004 | Matsuura et al. |
| 6,800,056 B2 | 10/2004 | Tartaglia et al. |
| 6,814,728 B2 | 11/2004 | Ouchi |
| 6,824,510 B2 | 11/2004 | Kim et al. |
| 6,827,718 B2 | 12/2004 | Hutchins et al. |
| 6,837,846 B2 | 1/2005 | Jaffe et al. |
| 6,866,626 B2 | 3/2005 | Long et al. |
| 6,869,393 B2 | 3/2005 | Butler |
| 6,911,005 B2 | 6/2005 | Ouchi et al. |
| 6,932,323 B2 | 8/2005 | James |
| 6,974,441 B2 | 12/2005 | Ravo |
| 7,056,283 B2 | 6/2006 | Baror et al. |
| 2002/0012059 A1 | 1/2002 | Wallerstein et al. |
| 2002/0072651 A1 | 6/2002 | Vilos |
| 2002/0107478 A1 | 8/2002 | Wendlandt |
| 2002/0109772 A1 | 8/2002 | Kuriyama et al. |
| 2002/0109773 A1 | 8/2002 | Kuriyama et al. |
| 2003/0000526 A1 | 1/2003 | Gobel |
| 2003/0074015 A1 | 4/2003 | Nakao |
| 2003/0083547 A1 | 5/2003 | Hamilton et al. |
| 2003/0105386 A1 | 6/2003 | Voloshin et al. |
| 2003/0168068 A1 | 9/2003 | Poole et al. |
| 2003/0181788 A1 | 9/2003 | Yokoi et al. |
| 2003/0191369 A1 | 10/2003 | Arai et al. |
| 2003/0208219 A1 | 11/2003 | Aznoian et al. |
| 2003/0225433 A1 | 12/2003 | Nakao |
| 2004/0004836 A1 | 1/2004 | Dubuc |
| 2004/0111010 A1 | 6/2004 | Nishiie |
| 2004/0143161 A1 | 7/2004 | Baror et al. |
| 2004/0199087 A1 | 10/2004 | Swain et al. |
| 2004/0199088 A1 | 10/2004 | Bakos et al. |
| 2004/0199196 A1 | 10/2004 | Ravo |
| 2004/0204702 A1 | 10/2004 | Ziegler et al. |
| 2004/0249247 A1 | 12/2004 | Iddan |
| 2004/0260150 A1 | 12/2004 | Bernstein |
| 2005/0038317 A1 | 2/2005 | Ratnakar |
| 2005/0038319 A1 | 2/2005 | Goldwasser et al. |
| 2005/0085841 A1 | 4/2005 | Eversull et al. |
| 2005/0095200 A1 | 5/2005 | Schwarzberg |
| 2005/0107664 A1 | 5/2005 | Kalloo et al. |
| 2005/0154355 A1 | 7/2005 | Gross et al. |
| 2005/0165272 A1 | 7/2005 | Okada et al. |
| 2006/0111611 A1 | 5/2006 | Eizenfeld et al. |

FOREIGN PATENT DOCUMENTS

| | | |
|---|---|---|
| EP | 0659387 | 6/1995 |
| JP | 7-313443 | 12/1995 |
| JP | 2006026344 | 2/2006 |
| WO | WO 00/44275 | 8/2000 |
| WO | WO 01/68540 | 9/2001 |
| WO | WO 02/059676 | 8/2002 |
| WO | WO 02/075348 | 9/2002 |
| WO | WO 03/026272 | 3/2003 |
| WO | WO 03/045487 | 6/2003 |
| WO | WO 03/046830 | 6/2003 |
| WO | WO 03/053225 | 7/2003 |
| WO | WO 2004/010858 | 2/2004 |
| WO | WO 2004/016299 | 2/2004 |
| WO | WO 2004/069057 | 8/2004 |
| WO | WO 2006/025045 | 3/2006 |

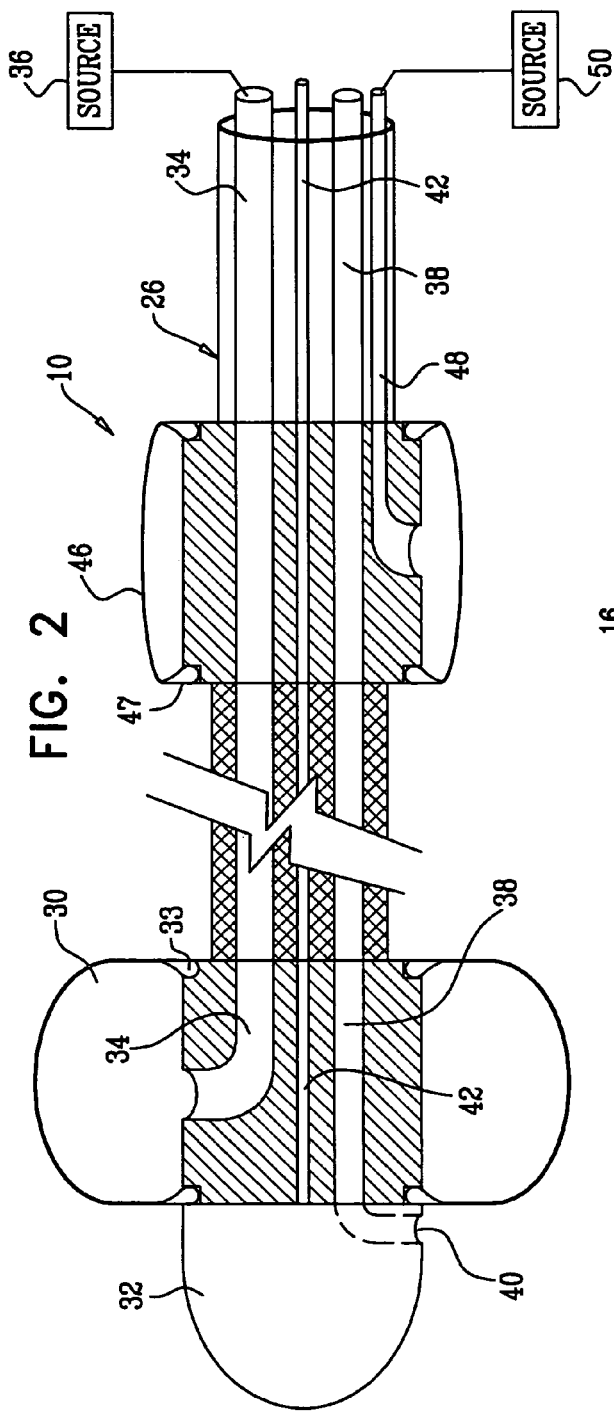
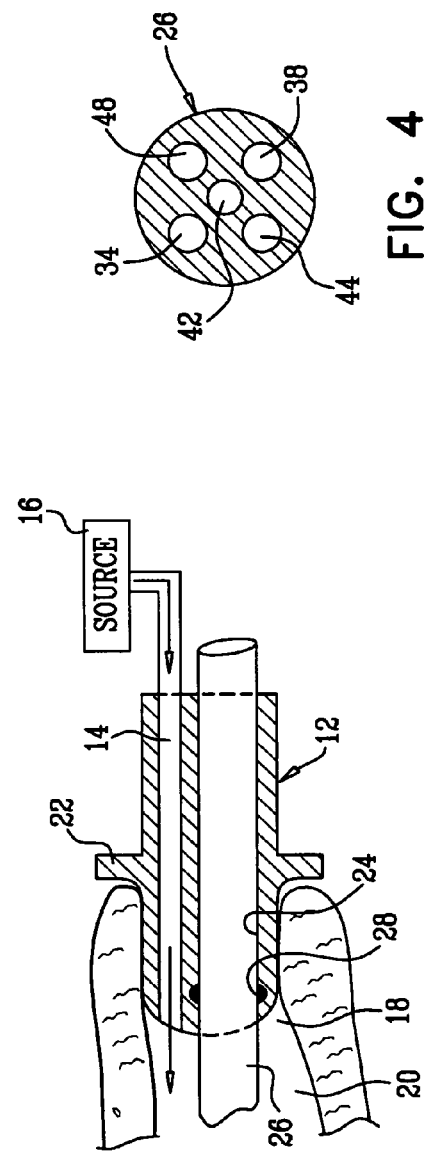

PRESSURE-PROPELLED SYSTEM FOR BODY LUMEN

FIELD OF THE INVENTION

The present invention relates generally to a pressure-propelled system, suitable for imaging body lumens, such as the gastrointestinal (GI) tract.

BACKGROUND OF THE INVENTION

Many imaging devices are known for producing medical images of body lumens, such as the gastrointestinal (GI) tract. For example, endoscopy is widely used for observing, photographing tissue, and taking specimens from lesions and the like. In a conventional method of examining a colon using an endoscope, for example, the endoscope is typically manually inserted into the colon. In this manual technique, patients may often complain of abdominal pain and distention because the colon is extended or excessively dilated, thereby necessitating stopping the endoscopic procedure. Furthermore, it is not unusual for the colon to bleed and be accidentally perforated. Insertion of an endoscope through the sigmoid colon and into the descending colon, or through the splenic flexure, the transverse colon, the hepatic flexure or parts affected by previous operations may also be accompanied with difficulty. Because of these reasons, a colonoscopy is typically performed by a relatively few number of skilled practitioners, and the rate of patient pain and discomfort is high.

U.S. Pat. No. 5,337,732 to Grundfest et al. describes a robot for performing endoscopic procedures, which includes a plurality of segments attached to each other through an articulated joint. Actuators can move the segments together and apart and change their angular orientation to allow the robot to move in an inchworm or snake-like fashion through a cavity or lumen within a patient. Inflatable balloons around the segments inflate to brace a temporarily stationary segment against the lumen walls while other segments move. A compressed gas line attached to the back segment provides compressed gas to inflate the balloons and optionally to drive the actuators. The lead segment includes a television camera and biopsy arm or other sensors and surgical instruments.

SUMMARY OF THE INVENTION

The present invention seeks to provide an improved imaging system which is propelled by fluid pressure, suitable for imaging body lumens, such as the gastrointestinal (GI) tract, as is described more in detail hereinbelow. The invention is described hereinbelow with reference to the GI tract, but it is understood that the invention is not limited to the GI tract and may be used for other body lumens as well. Unlike the prior art, which may inflate and anchor balloons and similar devices to the GI tract wall in an attempt to overcome the low friction of the GI tract, the present invention utilizes the very low friction environment of the GI tract to propel the imaging system, with no need for anchoring.

There is thus provided in accordance with an embodiment of the present invention, a system including a guide member at least partially insertable into a proximal opening of a body lumen, the guide member including a first passageway connectable to a source of fluid pressure, an elongate carrier arranged for sliding movement through the guide member, and a piston head mounted on the carrier, wherein a greater fluid pressure acting on a proximal side of the piston head than on a distal side of the piston head propels the piston head and the carrier in a distal direction in the body lumen.

The system of the invention may have different features. For example, the piston head may be inflatable. The carrier may include a second passageway in fluid communication with the piston head, which may be connected to a source of fluid pressure for inflating the piston head. A vent tube may pass through the piston head, having an opening distal to the piston head through which fluid may be vented to the outside. An image-capturing device may be mounted on the carrier, such as distal to the piston head. A power supply tube may pass through the carrier and may be connected to the image-capturing device. A fluid supply tube may pass through the carrier and may be connected to a fluid source.

In accordance with an embodiment of the present invention an auxiliary piston head may be mounted on the carrier proximal to the first-mentioned piston head. The auxiliary piston head, which may be inflatable, may be fixed axially to the carrier at a fixed distance from the first-mentioned piston head. The carrier may include a third passageway in fluid communication with the auxiliary piston head, which may be connected to a source of fluid pressure for inflating the auxiliary piston head.

BRIEF DESCRIPTION OF THE DRAWINGS

The present invention will be understood and appreciated more fully from the following detailed description taken in conjunction with the drawings in which:

FIGS. 2 and 3 are simplified sectional illustrations of distal and proximal portions, respectively, of the system of FIG. 1;

FIG. 4 is a simplified sectional illustration of a carrier of the system of FIG. 1, the section being taken transverse to a longitudinal axis of the carrier.

DETAILED DESCRIPTION OF EMBODIMENTS

Figure 1:
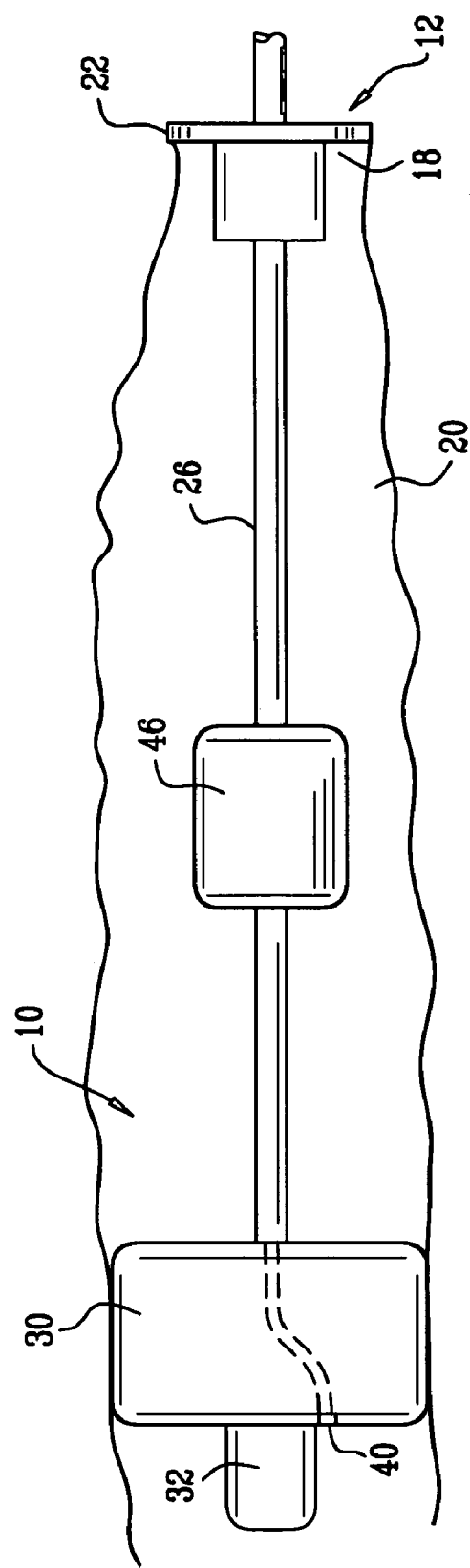
FIG. 1 is a simplified pictorial illustration of a system, constructed and operative in accordance with an embodiment of the present invention, which may be suitable for imaging body lumens, such as the GI tract.

Reference is now made to FIGS. 1-3, which illustrate a system 10, constructed and operative in accordance with an embodiment of the present invention.

As seen best in FIG. 3, system 10 may include a guide member 12, which may be constructed of any medically safe material, such as but not limited to, plastic or metal. Guide member 12 may be formed with a first passageway 14 connected to a source of fluid pressure 16, such as but not limited to, a source of pressurized air, $CO_2$ or water. Guide member 12 may be at least partially insertable into a proximal opening 18 (e.g., the rectum) of a body lumen 20 (e.g., the colon). Guide member 12 may include an annular ring 22 for abutting against the proximal opening 18.

Guide member 12 may be formed with a bore 24 through which an elongate carrier 26 may be arranged for sliding movement. An O-ring 28 may be provided for dynamically sealing carrier 26 in its sliding motion relative to the guide member 12. Carrier 26 may be any slender wire, catheter or tube and the like, constructed of any medically safe material, such as but not limited to, a flexible plastic or metal. Carrier 26, including its tip, may be safely deflected and steered through the body lumen 20.

A piston head 30 may be mounted on carrier 26. Piston head 30 may be inflatable, and as such may be constructed of any medically safe elastomeric material, such as but not limited to, a bladder or membrane made of polyurethane or silicone rubber, for example. An image-capturing device 32 may be mounted on carrier 26 distal to piston head 30. Piston head 30 is preferably fixed to carrier 26 and sealed thereto with O-rings 33, but optionally may be arranged to slide on carrier 26 up to some distal stop which arrests further distal motion of the piston head 30 (the image-capturing device 32 may serve as the distal stop, for example). Image-capturing device 32 may comprise, without limitation, a camera (e.g., CCD or CMOS), or alternatively x-ray, ultrasonic, MRI, infrared and/or microwave imaging devices.

Other therapeutic or diagnostic devices may be mounted on or in carrier 26, such as but not limited to, a magnet, drug delivery devices (e.g., iontophoresis), gene therapy devices and others.

The carrier 26 may include a second passageway 34 in fluid communication with piston head 30, connected to a source of fluid pressure 36 (e.g., pressurized air or water) for inflating piston head 30.

A vent tube 38 may pass through piston head 30, having an opening 40 distal to piston head 30 through which fluid is ventable to the outside (that is, the proximal end of vent tube 38 vents the fluid past guide member 12 to the outside). Optionally, the proximal end of vent tube 38 may be connected to a suction source (not shown) for sucking fluid through vent tube 38.

A power supply tube 42 (e.g., containing electrical wires, fiber optics, etc.) may pass through carrier 26, for connection to image-capturing device 32. Alternatively, the electrical and optical components of image-capturing device 32 may have their own internal power source, with no need for external wiring. The image-capturing device 32 may wirelessly transmit or receive data to or from an external processor (not shown). The components of system 10 may be fully automated with sensors and operate in a closed or open control loop.

A fluid supply tube 44 (seen in FIG. 4 only) may pass through carrier 26, which may be connected to a fluid source (not shown), e.g., pressurized water, for cleaning the area near the image-capturing device 32, or in combination with the vent tube 38, for cleaning the body lumen 20 itself (e.g., the colon).

In accordance with an embodiment of the present invention an auxiliary piston head 46 may be mounted on the carrier proximal to the distal piston head 30. The auxiliary piston head 46, which like the piston head 30 may be inflatable, may be fixed axially to carrier 26 at a fixed distance from piston head 30. Auxiliary piston head 46 may be sealed with respect to carrier 26 with O-rings 47. The carrier 26 may include a third passageway 48 in fluid communication with auxiliary piston head 46, connected to a source of fluid pressure 50 for inflating auxiliary piston head 46.

Reference is now made to FIGS. 1, 2 and 5-7, which illustrate operation of the system 10, in accordance with an embodiment of the present invention. The system 10 may be inserted in the rectum with the piston heads 30 and 46 initially deflated to facilitate insertion. The distal piston head 30 may then be gently inflated until it expands to the inner walls of the body lumen (e.g., colon) 20 (the configuration shown in FIG. 1). Pressurized fluid (e.g., air) from the source of fluid pressure 16 may be introduced into the colon through the first passageway 14 of guide member 12. The pressurized fluid creates greater fluid pressure acting on the proximal side of piston head 30 than on the distal side of piston head 30. The vent may assist in creating the pressure difference across the piston head 30. This pressure difference propels piston head 30 together with carrier 26 distally into the body lumen (in this example, the colon), as indicated by arrow 60. Image-capturing device 32 may capture images of the body lumen 20 as the system 10 travels therethrough.

Figure 5:
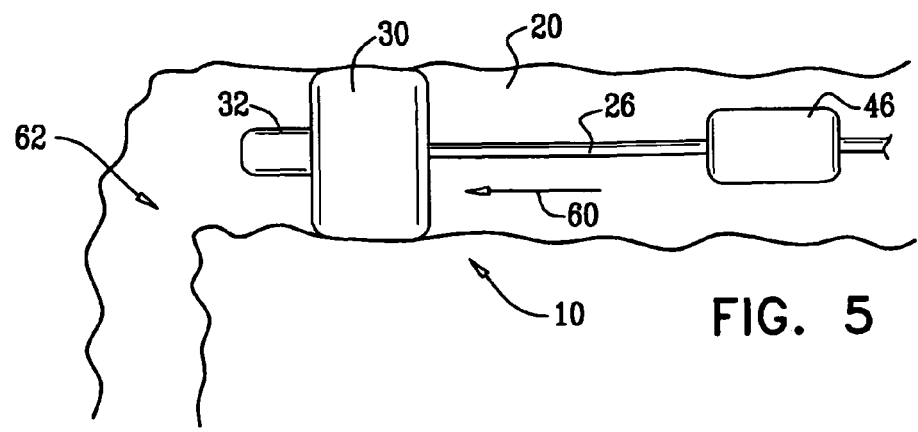
FIGS. 5, 6 and 7 are simplified pictorial illustrations of the system of FIG. 1, showing three steps of a mode of operation thereof, wherein inflatable piston heads are inflated and deflated to negotiate obstacles in a body lumen.
Figure 6:
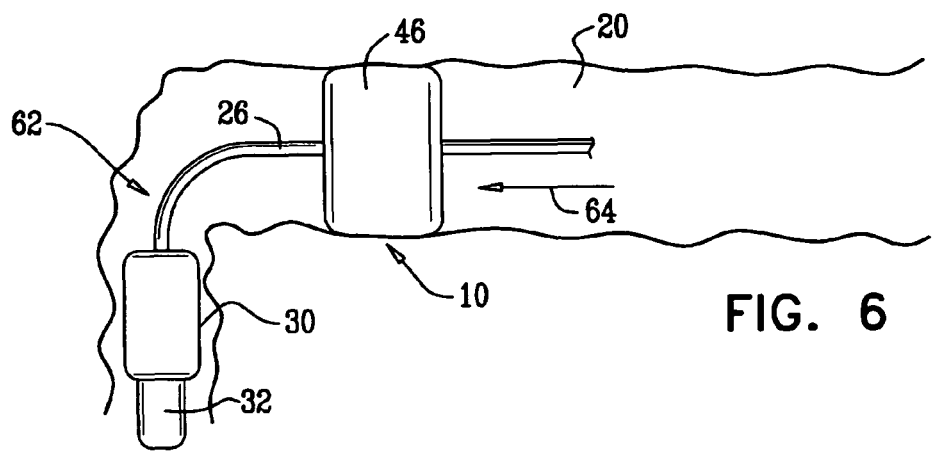
Figure 7:
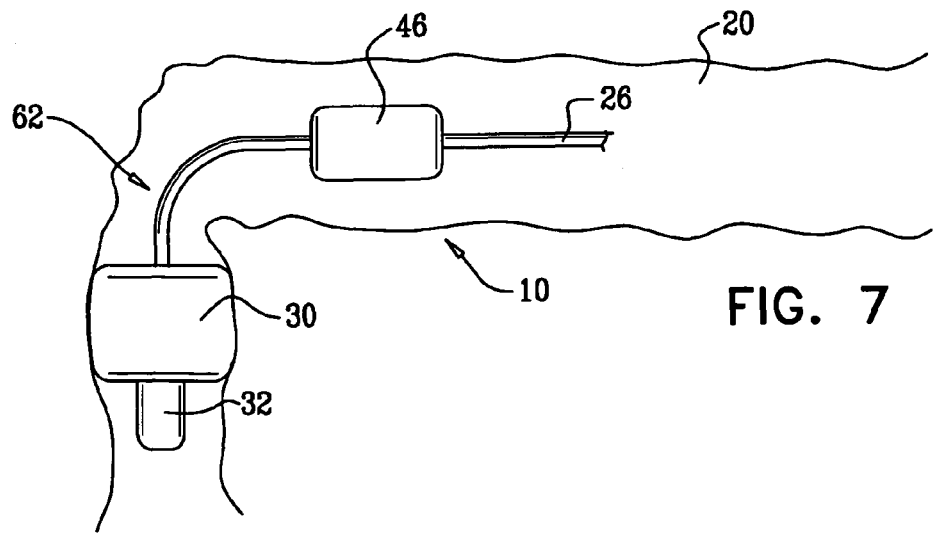

As seen in FIG. 5, the system 10 may eventually reach an obstacle or tight turn, indicated by arrow 62. In such a case, the proximal piston head 46 may be inflated and the distal piston head 30 may be deflated as shown in FIG. 6. In this configuration, the pressurized fluid creates greater fluid pressure acting on the proximal side of the proximal piston head 46 than on the distal side of the proximal piston head 46. This pressure difference propels the proximal piston head 46 together with carrier 26 distally, as indicated by arrow 64. This distal movement brings the distal deflated piston head 30 past the obstacle, as seen in FIG. 6. The system 10 continues its distal movement in the body lumen 20 until the proximal piston head 46 reaches the obstacle. At this point, the distal piston head 30 may be inflated and the proximal piston head 46 may be deflated once again, as shown in FIG. 7. Once again, the pressurized fluid creates greater fluid pressure acting on the proximal side of the distal piston head 30 than on the distal side of the distal piston head 30. The pressure difference propels the system 10 distally in the body lumen 20, and brings the proximal deflated piston head 46 past the obstacle. The cycle may be repeated as often as necessary.

Although the invention has been described in conjunction with specific embodiments thereof, many alternatives, modifications and variations are apparent to those skilled in the art. Accordingly, all such alternatives, modifications and variations fall within the spirit and scope of the following claims.

What is claimed is:

1. A system for use with a source of fluid pressure, comprising:
   a guide member at least partially insertable into a proximal opening of a body lumen, said guide member is formed with a passageway connectable to the source of fluid pressure and operable to convey the fluid pressure into the lumen when the guide member is inserted into the body lumen, said guide member thereby allowing application of said fluid pressure upon the inner walls of the body lumen;
   an elongate carrier arranged for sliding movement through said guide member;
   and an inflatable piston head mounted on said carrier,
   a fluid lumen provided within said elongate carrier connected between said piston head and the source of fluid pressure for inflating said piston head,
   the piston head having a proximal side and a distal side and configured such that once the piston head is inflated it is configured to be advanced distally in the body lumen, due to a fluid pressure difference between the fluid pressure acting on the proximal end of the piston head and a fluid pressure acting on the distal side thereof, thereby propelling said piston head together with said carrier distally into the lumen.

2. The system according to claim 1, further comprising a vent tube passing through said piston head, having an opening distal to said piston head through which fluid is ventable to outside of said body lumen.

3. The system according to claim 1, further comprising an image-capturing device mounted on said carrier.

4. The system according to claim 3, wherein said image-capturing device is distal to said piston head.

5. The system according to claim 3, further comprising a power supply tube passing through said carrier and connected to said image-capturing device.

6. The system according to claim 1, further comprising an auxiliary piston head mounted on said carrier proximal to the piston head.

7. The system according to claim 6, wherein said auxiliary piston head is fixed axially to said carrier at a fixed distance from the piston head.

8. The system according to claim 6, wherein said auxiliary piston head is inflatable.

9. The system according to claim 8, wherein said carrier includes an auxiliary-piston-head passageway in fluid communication with said auxiliary piston head and connectable to an auxiliary-piston-head source of fluid pressure for inflating said auxiliary piston head.

10. The system according to claim 1, wherein said fluid pressure difference is due to the fluid pressure conveyed into the lumen by the passageway impinging on a proximal side of said piston head and being greater than a fluid pressure present on a distal side of said piston head.

11. The system according to claim 1, wherein said piston head expands to the inner wall of said body lumen after said piston head has been inflated.

\* \* \* \* \*